(12) United States Patent
Ohnishi et al.

(10) Patent No.: US 7,052,917 B1
(45) Date of Patent: May 30, 2006

(54) POLYMERIZABLE BIOTIN DERIVATIVES, BIOTIN POLYMER, AND POLYMER RESPONSIVE TO AVIDIN STIMULATION

(75) Inventors: Noriyuki Ohnishi, Kanagawa (JP); Mikiko Yoshida, Ibaraki (JP); Kazunori Kataoka, Tokyo (JP); Katsuhiko Ueno, Ibaraki (JP)

(73) Assignees: National Institute of Advanced Industrial Science and Technology, Tokyo (JP); Japan Chemical Innovation Institute, Tokyo (JP)

( * ) Notice: Subject to any disclaimer, the term of this patent is extended or adjusted under 35 U.S.C. 154(b) by 619 days.

(21) Appl. No.: 10/048,230

(22) PCT Filed: Jul. 28, 2000

(86) PCT No.: PCT/JP00/05113

§ 371 (c)(1),
(2), (4) Date: Jan. 29, 2002

(87) PCT Pub. No.: WO01/09141

PCT Pub. Date: Feb. 8, 2001

(30) Foreign Application Priority Data

Jul. 29, 1999 (JP) .................................. 11-215667

(51) Int. Cl.
*G01N 33/545* (2006.01)
*C07K 17/08* (2006.01)

(52) U.S. Cl. ........................ 436/531; 435/7.5; 436/532; 530/391.7

(58) Field of Classification Search ................. 435/7.5, 435/188; 436/531, 532; 530/391.7
See application file for complete search history.

(56) References Cited

U.S. PATENT DOCUMENTS

| | | | |
|---|---|---|---|
| 5,795,719 A | 8/1998 | Richard et al. | |
| 5,863,748 A | 1/1999 | Bobrow | |
| 6,207,369 B1 | 3/2001 | Wohlstadter et al. | |

FOREIGN PATENT DOCUMENTS

| | | | |
|---|---|---|---|
| BE | 898664 | * | 5/1984 |
| EP | 11777 | | 6/1980 |
| EP | 178791 | * | 4/1986 |
| EP | 226470 | | 6/1987 |
| EP | 914835 | | 5/1999 |
| EP | 922715 | | 6/1999 |
| JP | 2-96581 | | 4/1990 |
| JP | 9-49830 | | 2/1997 |
| WO | 86/1899 | | 3/1986 |
| WO | 95/31730 | | 11/1995 |
| WO | 96/4402 | | 2/1996 |
| WO | 97/329 | | 1/1997 |
| WO | 99/64378 | | 12/1999 |

OTHER PUBLICATIONS

R. Roy et al, J. Chem. Soc., Chem. Commun., [1992] pp. 1611-1613.*
G. Sigal et al, J. Amer. Chem. Soc., [1996] vol. 118, No. 16, pp. 3789-3800.*
Morris et al., "Affinity precipitation of proteins by polyligands.", Database Biosis Online! Biosciences Information Services, Philadelphia, PA, US 1993, Database accession No. PREV199395116256, XP002211217, abstract.
Hoffman et al., "Founder's Award, Society for Biomaterials. Sixth World Biomaterials Congress 2000, Kamuela, HI, May 15-20, 2000. Really smart bioconjugates of smart polymers and receptor proteins.", Journal of Biomedical Materials Research. United States, Dec. 15, 2000, vol. 52, No. 4, pp. 577-586.
Tarasow, T., et al. "Characteristics of an RNA Diels-Alderase Active Site", J. Am. Chem. Soc., vol. 121, No. 15 (1999), pp. 3614-3617.
Nelson, P., et al. "Convenient preparation of new C-5 biotinylated dUTP derivative", Nucleosides Nucleotides, vol. 5, No. 3 (1986), pp. 233-241.

* cited by examiner

*Primary Examiner*—Mary E. Ceperley
(74) *Attorney, Agent, or Firm*—Wenderoth, Lind & Ponack, L.L.P.

(57) ABSTRACT

The present invention is to prepare a novel polymerizable biotin derivative represented by formula (I) shown below and make it possible to synthesize or design a polyfunctional or multifunctional polymer using the derivative.

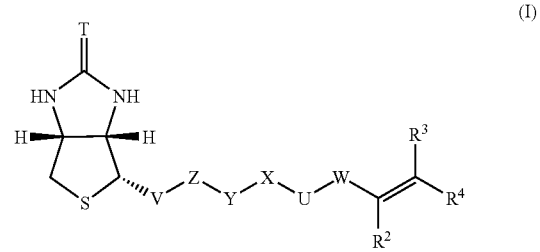

(I)

In formula (I), $R^2$ represents a hydrogen atom or an alkyl group, $R^3$ and $R^4$ each independently represents a hydrogen atom, an alkyl group or an aryl group, T represents an oxygen atom or =NH, W represents a single bond, a carbonyl group, a thiocarbonyl group or a $C_{1-5}$ alkylene group, U represents a single bond or —NH—, X represents a single bond, a $C_{1-8}$ hydrocarbon bond, an oxygen atom or —NH—, Y represents a single bond, a carbonyl group, a thiocarbonyl group, —NH—, a 1,2-dioxyethylene group or a 1,2-diaminoethylene group, Z represents a single bond, a carbonyl group, a thiocarbonyl group, a $C_{1-5}$ alkylene group, an oxygen atom or —NH—, and V represents a single bond or a $C_{1-5}$ alkylene group.

3 Claims, No Drawings

POLYMERIZABLE BIOTIN DERIVATIVES, BIOTIN POLYMER, AND POLYMER RESPONSIVE TO AVIDIN STIMULATION

This application is a 371 application of PCT/JP00/05113 filed Jul. 28, 2000.

TECHNICAL FIELD

The present invention provides an excellent technique as an immobilizing method of (imino)biotin derivatives which has recently enjoyed wide spread adoption. The invention further relates to provision of a functional polymer which has an (imino)biotin site immobilized using the derivative.

BACKGROUND ART

A technique making use of high biotin-avidin affinity (see, for example, "Methods Enzymol, 184, 5-(13, and 184, 14-(45) has been applied to immunoassays (for example, Japanese Patent Laid-Open Nos. Hei 4-363659 and Hei 6160387), biosensors (for example, Japanese Patent Laid-Open Nos. Hei 10-282040, Hei 9-292397 and Hei 8-94510), DNA operations (for example, Japanese Patent Laid-Open No. Hei 4-267896), separating materials (for example, Japanese Patent Laid-Open Nos. Hei 5-340945 and Hei 4-311397), and clinical therapies (for example, J. Nucl. Med. Commun., 12, 211–234(1991), and Int. J. cancer, 45, 1184–1189(1990)).

The above-described various methods need immobilization of biotin to a protein (glycoprotein), antibody, enzyme, chromophore, dextran or the like and for this purpose, various biotin immobilizing reagents have been put on the market (Methods Enzymol., 184, 123–138). These reagents serve to immobilize biotin to a biological material by reacting them with its reactive functional group such as amino group, sulfur group, carboxylic acid or alcohol (see, for example, "Molecular Probes Handbook of Fluorescent Probes and Research Chemicals, Chapter 4") Biotin derivatives are employed for such an immobilizing reaction (see, for example, Molecular Probes Handbook of Fluorescent Probes and Research Chemicals, Chapter 4, p87). Immobilization of biotin to the terminal of polyethylene glycol by using these reagents has also been reported (Bioconjugate Chem., 8, 545–551(1997)).

The above-described immobilization of biotin is carried out based on the concept that biotin is immobilized by conducting one reaction with one functional group of an originally existing substance such as protein (see, for example, Japanese Patent Laid-Open No. Hei 6-148190).

Usefulness of biotin has thus been verified in various fields and there is a possibility of its industrial application leading to development of products exhibiting a new function. The above-described biotin immobilizing reagents are however expensive, which prevents industrial use thereof for immobilization of biotin. In addition, there is an eager demand for appearance of a heat sensitive polymer which aggregates in an aqueous solution or physiological saline by a cooling operation and exhibits an upper critical solution temperature (UCST), because its application to a separating agent or DDS is expected (Macromol. Chem., Rapid Commun., 13, 577–581(1992)).

The biotin immobilizing reagents immobilize biotin to a reactive functional group as described above so that protection of the functional group is sometimes necessary. Biotin immobilizing reaction itself is difficult in the case of immobilization to a functional group having large steric hindrance or immobilization of a biotin skeleton to a polymer chain. For example, when biotin is immobilized to a protein which is a macro molecule, deficiency of its functional groups prevents immobilization of a sufficient amount of biotin and in addition, biotin is immobilized only to the functional groups existing on the surface of the protein. The higher the polymerization degree of a polymer, the more difficult it becomes to immobilize biotin as desired by the conventional immobilizing method.

Accordingly, an object of the present invention is to synthesize or design a polyfunctional or multifunctional biotin-component-containing polymer applicable to various fields.

Another object of the invention is to industrially produce the biotin-component-containing polymer and to synthesize or design it in excellent economies and efficiency.

A further object of the present invention is to provide a heat sensitive polymer which aggregates in an aqueous solution by a cooling operation and exhibits an upper critical solution temperature (UCST) even in physiological saline; and a heat sensitive polymer which aggregates in an aqueous solution by a heating operation and has a lower critical solution temperature (LCST) in an aqueous solution.

DISCLOSURE OF THE INVENTION

It was found that the above-described objects can be attained by the use of a polymerizable biotin derivative represented by the following formula (I):

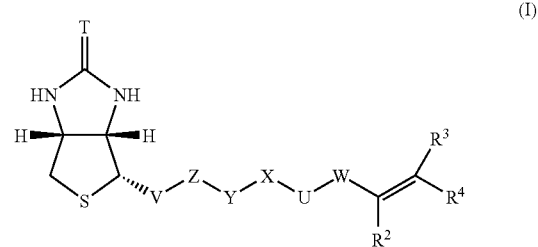

In formula (I), $R^2$ represents a hydrogen atom or an alkyl group. $R^3$ and $R^4$ each independently represents a hydrogen atom, an alkyl group or an aryl group.

T represents an oxygen atom or $=$NH.

W represents a single bond, a carbonyl group, a thiocarbonyl group or a $C_{1-5}$ alkylene group. U represents a single bond or —NH—. X represents a single bond, a $C_{1-8}$ hydrocarbon bond, an oxygen atom or —NH—. Y represents a single bond, a carbonyl group, a thiocarbonyl group, —NH—, a 1,2-dioxyethylene group or a 1,2-diaminoethylene group. Z represents a single bond, a carbonyl group, a thiocarbonyl group, a $C_{1-5}$ alkylene group, an oxygen atom or —NH—. V represents a single bond or a $C_{1-5}$ alkylene group.

In the invention, polymerization of the polymerizable biotin derivative (which may hereinafter be simply called "biotin monomer") having a biofunction makes it possible to industrially and economically synthesize the corresponding polymer having (imino)biotin immobilized thereto (the term "biotin" as used herein embraces the meaning of iminobiotin unless otherwise specifically indicated by the name of a compound).

A biotin monomer having biotin immobilized thereto has, as a starting material, economies and efficiency enabling industrial production.

The invention method differs from the known biotin immobilizing technique such as immobilization of biotin to a polymer by reacting its functional group so that even copolymerization with a monomer having a functional group reactive with a biotin immobilizing reagent makes it possible to synthesize the corresponding copolymer having biotin immobilized to the copolymer but containing the functional group remained unreacted.

Even in the case where the conventional biotin immobilization technique cannot be adopted because the functional group is enclosed in a high molecular chain, appropriate designing of a polymer makes it possible to integrate therein a biotin skeleton as a long polymer chain at any ratio.

For example, a thermo-responsive polymer having a biotin or iminobiotin site and exhibiting a lower critical solution temperature (LCST) or upper critical solution temperature (UCST) in an aqueous solution was found. It was found that a polymer obtained by copolymerizing the polymerizable biotin derivative of the invention with at least one monomer component selected from acrylamide and methacrylamide is a heat sensitive polymer compound having UCST (upper critical solution temperature) in an aqueous solution or physiological saline.

It was also found that by immobilizing biotin to a thermo-responsive polymer having LCST, the thermo-responsive polymer acquires markedly high aggregation force at the LCST or greater.

Since these polymers have biotin immobilized thereto, various avidin immobilized ligands and, through four binding sites of avidin, various biotinylated ligands can be immobilized to them readily. The term "avidin" as used herein embraces the meaning of streptavidin.

The thermo-responsive polymer derivatives of the invention are thermo-responsive to a large aggregation force at LCST or greater or at UCST or less in an aqueous solution, physiological saline or buffer so that they can be used effectively for separation, enzymatic immobilization, weighing or control of various substances.

BEST MODE FOR CARRYING OUT THE INVENTION

The present invention is described in detail below.

In the polymerizable biotin derivative represented by formula (I), it is preferred that $R^2$ represents a hydrogen atom or a $C_{1-3}$ alkyl group, and $R^3$ and $R^4$ each represents a hydrogen atom, a $C_{1-3}$ alkyl group or a phenyl group. It is particularly preferred that $R^2$ represents a hydrogen atom or a methyl group, and $R^3$ and $R^4$ each represents a hydrogen atom, a methyl group or a phenyl group. The alkyl or aryl group may have a substituent if necessary.

Specific examples of the binding group represented by —V—Z—Y—X—U—W— in formula (I) include those exemplified below in Table-1.

TABLE-1

| Ex. | V | Z | Y | X | U | W |
|---|---|---|---|---|---|---|
| (1) | $C_{1-5}$ Alkyl group | Oxygen atom or —NH— | Carbonyl or thio-carbonyl group | Single bond | Single bond | Single bond |
| (2) | $C_{1-5}$ Alkyl group | Oxygen atom or —NH— | Carbonyl or thio-carbonyl group | Oxygen atom or —NH— | Single bond | Carbonyl or thio-carbonyl group |

TABLE-1-continued

| Ex. | V | Z | Y | X | U | W |
|---|---|---|---|---|---|---|
| (3) | $C_{1-5}$ Alkyl group | Single bond | Carbonyl or thio-carbonyl group | 1,2-Dioxy-ethylene or 1,2-di-amino-ethylene group | Single bond | Carbonyl or thio-carbonyl group |
| (4) | $C_{1-5}$ Alkyl group | Single bond | Single bond | Single bond | Single bond | Single bond |
| (5) | $C_{1-5}$ Alkyl group | Single bond | Single bond | Oxygen atom or —NH— | Single bond | Single bond |
| (6) | $C_{1-5}$ Alkyl group | Carbonyl group | —NH— | $C_{1-8}$ Hydrocarbon bond | —NH— | Carbonyl group |

More preferred polymerizable biotin derivatives of formula (I) include those of the following formulas (1a) to (1c):

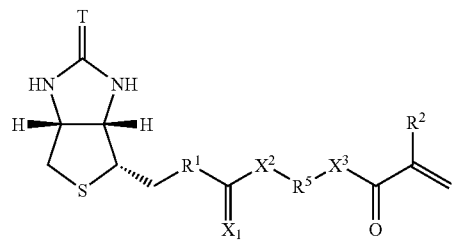

(Ia)

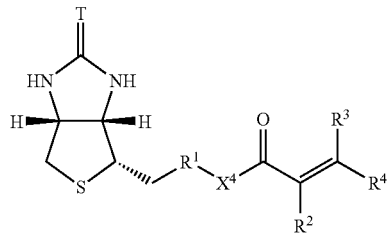

(Ib)

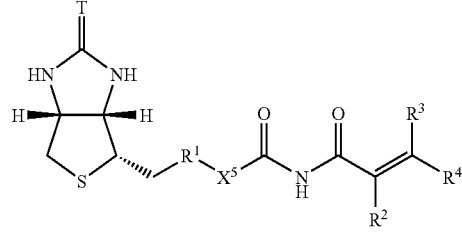

(Ic)

In formulas (Ia) to (Ic), $R^1$ represents a single bond or a $C_{1-4}$ alkylene group and $R^5$ represents a $C_{2-3}$ alkylene group.
$X^1$ represents an oxygen or sulfur atom and $X^2$ to $X^5$ each independently represents an oxygen atom or —NH—.
T, $R^2$, $R^3$ and $R^4$ each has the same meaning as defined in formula (I).

In formula (Ia), it is preferred that $R^1$ represents a $C_{1-5}$ alkylene group, more preferably a $C_{2-4}$ alkylene group, $R^5$ represents a $C_{2-3}$ alkylene group, $R^2$ preferably represents a hydrogen atom or a methyl group, $X^1$ represents an oxygen or sulfur atom, and $X^2$ and $X^3$ each independently represents an oxygen atom or —NH—. T represents an oxygen atom or =NH.

In formula (Ib), it is preferred that $R^1$ represents a $C_{1-5}$ alkylene group, more preferably a $C_{2-4}$ alkylene group, $R^2$ preferably represents a hydrogen atom or a methyl group, and $R^3$ and $R^4$ each independently represents a hydrogen atom, an alkyl group or an aryl group, more preferably a hydrogen atom. $X^4$ preferably represents an oxygen atom or —NH—. T represents an oxygen atom or =NH.

In formula (Ic), it is preferred that $R^1$ represents a $C_{1-5}$ alkylene group, more preferably, a $C_{2-4}$ alkylene group, $R^2$ preferably represents a hydrogen atom or a methyl group, and $R^3$ and $R^4$ each independently represents a hydrogen atom, an alkyl group or an aryl group, more preferably a hydrogen atom. $X^5$ preferably represents an oxygen atom or —NH—. T represents an oxygen atom or =NH.

The polymerizable biotin derivative represented by formula (Ia) can be obtained by converting the side chain carboxyl hydroxyl group of biotin or a biotin derivative of formula (a1) shown below into a proper eliminating group, followed by condensation with an acrylic derivative represented by formula (a2) shown below.

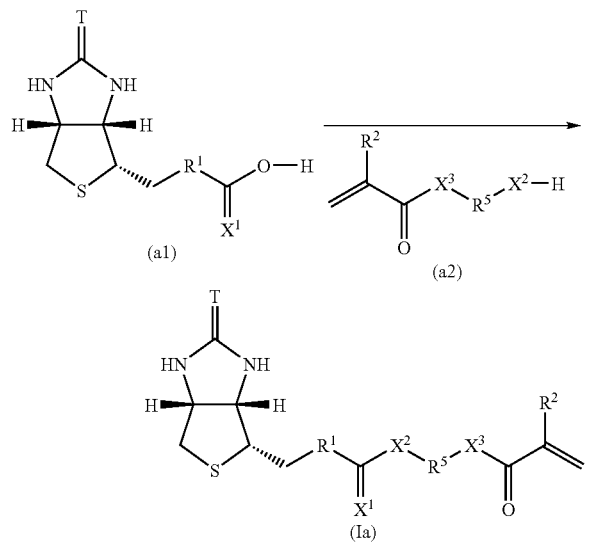

Its specific process will next be described.

For example, after reflux of the carboxyl group of biotin (i) shown below in thionyl chloride/toluene for 2 hours, the reaction mixture is subjected to condensation reaction with 2-hydroxyethyl acrylate (ii), whereby 2-biotinylethyl acrylate (A) can be obtained.

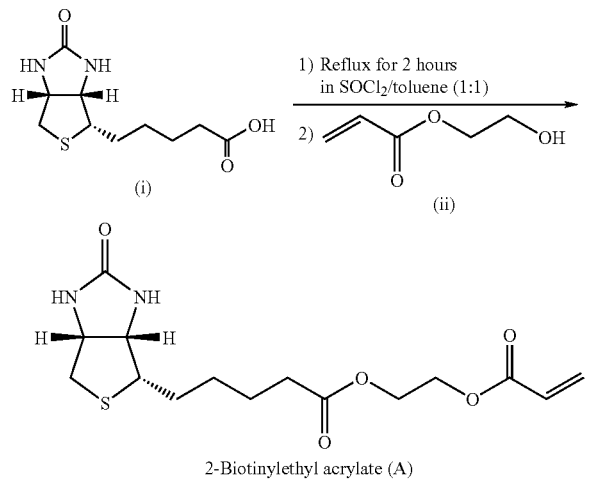

2-Biotinylethyl acrylate (A)

By reacting (imino)biotin (i') with N—(3-aminopropyl) methacrylamide hydrochloride (iii) in the presence of diphenylphosphonyl azide (DPPA), triethylamine (TEA) and N,N-dimethylformamide (DMF), N-biotinyl-N'(meth)acroyltrimethylene amide (B) or N-iminobiotinyl-N'(meth) acroyltrimethylene amide (C) can be obtained.

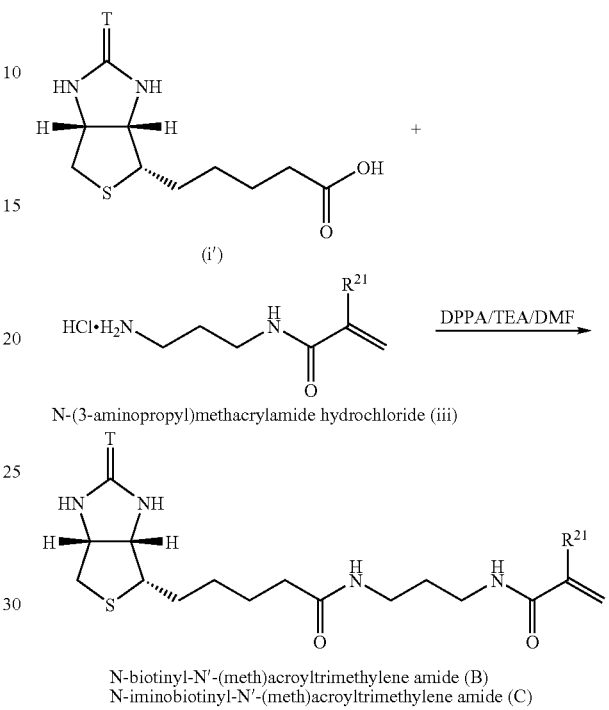

N-biotinyl-N'-(meth)acroyltrimethylene amide (B)
N-iminobiotinyl-N'-(meth)acroyltrimethylene amide (C)

(wherein $R^{21}$ represents a hydrogen atom or a methyl group)

The polymerizable biotin derivative represented by formula (Ib) can be usually obtained by reacting the biotin derivative of formula (b1) shown below with an appropriate acrylating agent (b2) (including a methacrylating agent. Examples include acrylating agents such as acrylic acid, acrylic acid chloride, acrylic anhydride and acryloxysuccinimide and methacrylating agents such as methacrylic acid, methacrylic acid chloride, methacrylic anhydride and methacryloxysuccinimide).

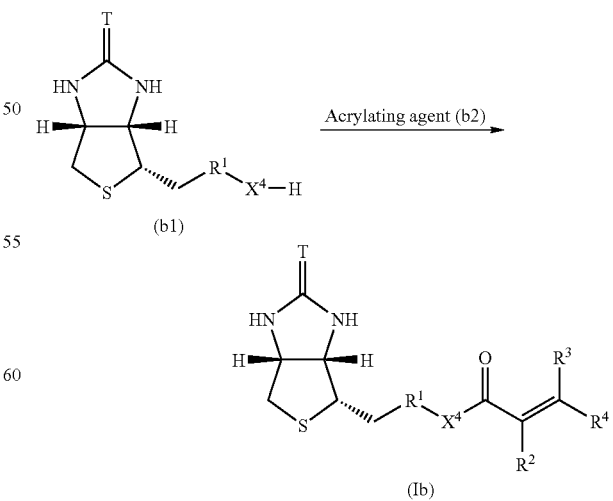

In the above formula, the biotin derivative of formula (b1) can be obtained by reducing the biotin or biotin derivative of formula (a1) with an appropriate reducing agent into the corresponding alcohol derivative (wherein $X^4$=an oxygen atom), converting the hydroxyl group of the alcohol derivative into a functional group having a function of an eliminating group, and then subjecting the resulting compound to substitution reaction with an amine derivative (wherein $X^4$=—NH—).

This process will next be described more specifically.

For example, as described below, commercially available biotin (product of Merck & Co., Inc.) is reduced into biotinol (iv) with a reducing agent such as sodium borohydride, diisobutyl aluminum hydride, THF borane or lithium aluminum hydride (Flaster and Kohn, J. Heterocycl. Chem. 18(7), 1425–36(1981)). The resulting biotinol (iv) is reacted with an acrylating agent, followed by recrystallization, whereby biotinol acrylate (D) can be obtained.

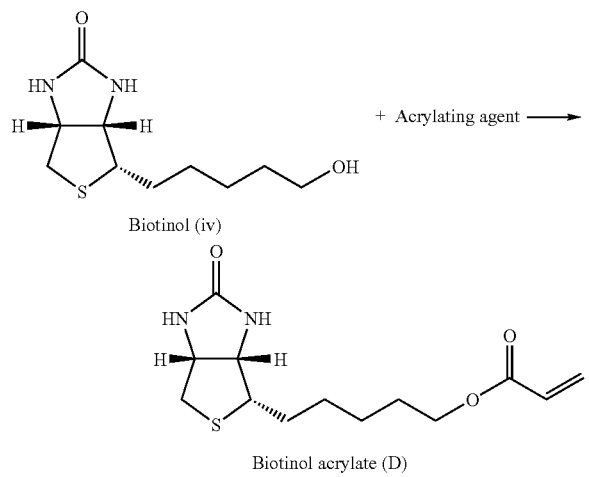

Biotinol methacrylate (E) can be obtained by reacting the biotinol (iv) with a methacrylating agent.

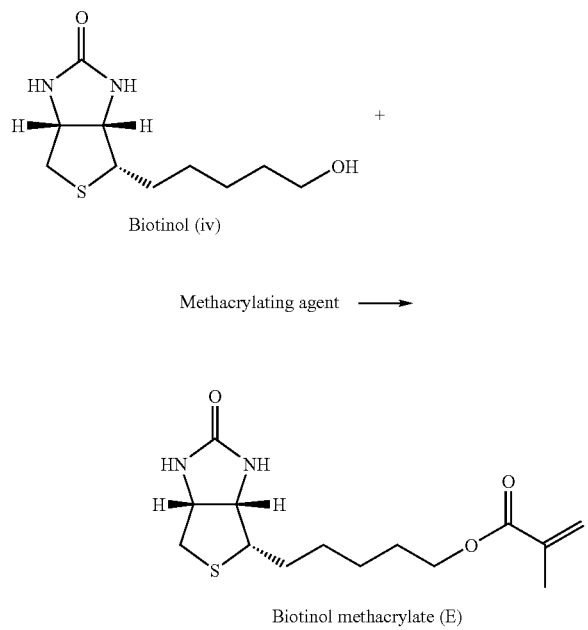

As described below, after conversion of the hydroxyl group of the biotinol (iv) into a functional group having an eliminating function, substitution reaction with an amine derivative is effected to obtain biotin amine (V). The biotin amine or salt thereof is then reacted with an acrylating agent in the presence of a condensing agent (such as diethylphosphoric acid cyanide or diphenylphosphoric acid azide), whereby biotinamine acrylamide (F) can be obtained.

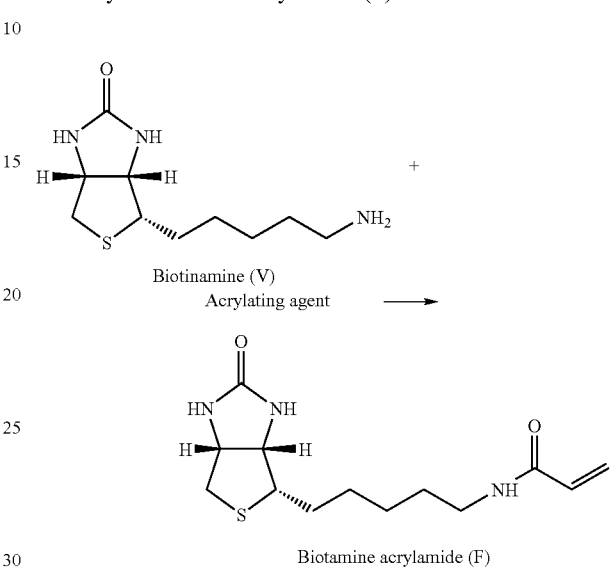

Similarly, biotinamine (v) or salt thereof is reacted with a methacrylating agent in the presence of a condensing agent (such as diethylphosphoric acid cyanide or diphenylphosphoric acid azide), whereby biotinamine methacrylamide (G) can be obtained.

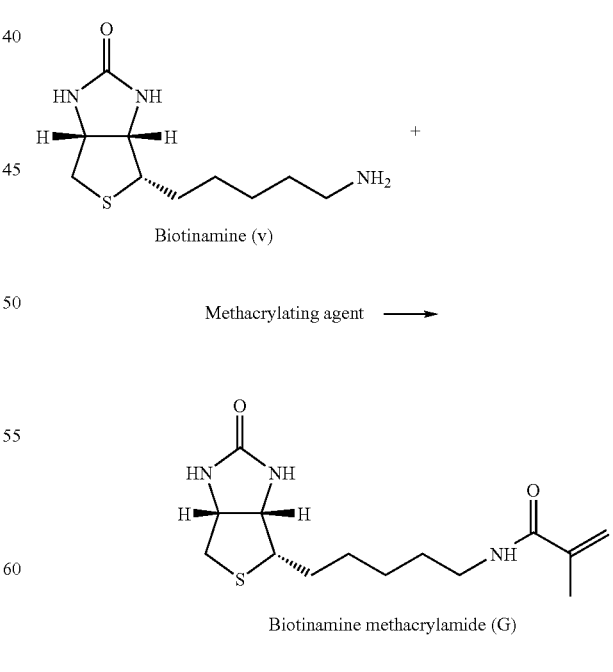

As described below, norbiotinamine (vi) or salt thereof is reacted with an acrylating agent in the presence of a condensing agent (such as diethylphosphoric acid cyanide or diphenylphosphoric acid azide), whereby norbiotinamine acrylamide (H) can be obtained.

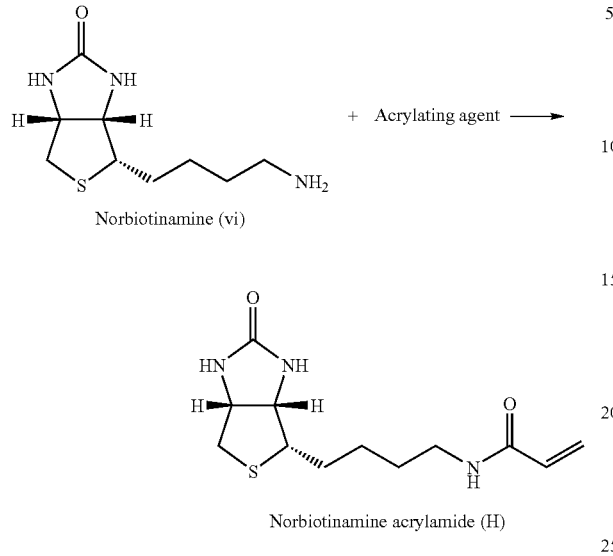

In a similar manner to that described above, norbiotinamine (vi) or salt thereof is reacted with methacrylic acid in the presence of a condensing agent (such as diethylphosphoric acid cyanide or diphenylphosphoric acid azide), whereby norbiotinamine methacrylamide (J) can be obtained.

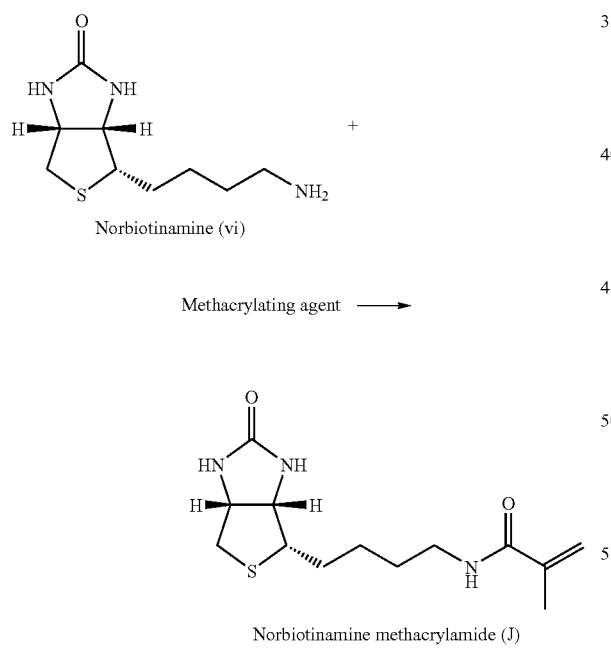

The polymerizable biotin derivative represented by formula (Ic) can be obtained by reacting a biotin derivative represented by formula (c1) shown below with an isocyanate compound represented by formula (c2) in an aprotic solvent such as TMF, DMSO, ether, DMF, dichloromethane, chloroform, ethyl acetate, acetone, aliphatic hydrocarbon, benzene or toluene.

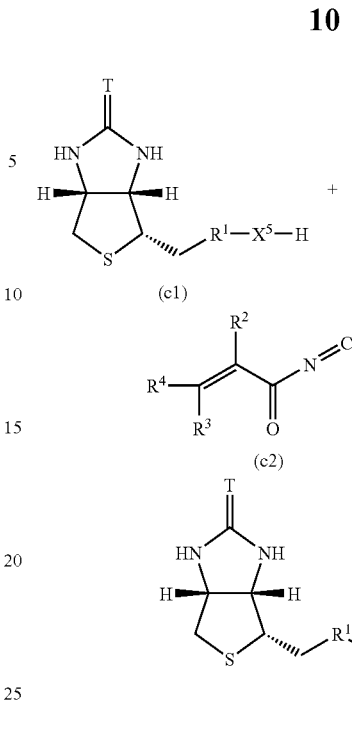

Described specifically, for example, biotinol methacryloyl carbamate (K) can be obtained by reacting biotinol (iv) with methacroyl isocyanate (vii) in a solvent such as methylene chloride.

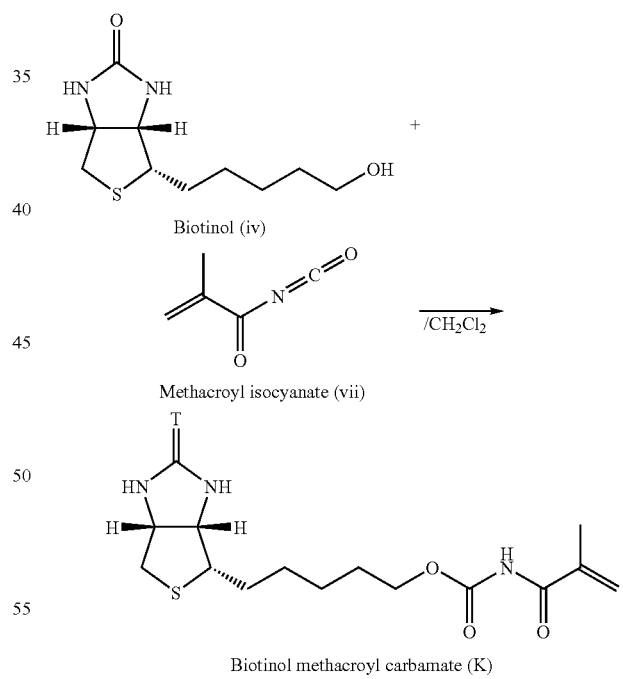

By polymerizing the novel polymerizable biotin derivatives (biotin monomers) of the invention thus obtained alone or together with a monomer copolymerizable therewith in a conventional manner in the presence of an appropriate radical polymerization initiator, for example, in a solvent in which they are soluble, biotin-component-containing polymer derivatives (which may hereinafter be simply called "biotin polymers") can be obtained. This makes it possible to industrially and readily produce highly useful polymer compounds having biotin immobilized thereto. The term "biotin component" as used herein means a portion having a high affinity with avidin (including streptavidin), more specifically, a component (biotin component or iminobiotin component) represented by formula (II) shown below.

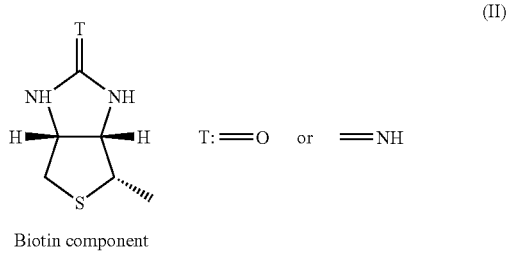

Biotin component

In the invention, copolymerization with any another monomer component enables the synthesis or designing of a biotin polymer equipped with a function of this monomer component. This leads to synthesis of a polyfunctional or multifunctional polymer. Thus, polymerization with this biotin monomer makes it possible to produce a biotin polymer which can utilize usefulness of a biotin monomer while making use of the properties of the polymer itself, thus having synergistic effects.

No particular limitation is imposed on the component copolymerizable with the polymerizable biotin derivatives insofar as it is polymerizable. As the component, vinyl, vinylidene, butadiene and the like polymerizable monomers are usable. Specific examples include acrylamide, methacrylamide, styrene, N-alkyl acrylamide, methyl acrylate, vinyl acetate, methacrylonitrile methyl methacrylate and isoprene. There is no particular limitation imposed on the copolymerization ratio and these monomers may be copolymerized at any ratio according to the need.

After reaction, the polymer derivatives are preferably purified in a usual manner. The purification can be carried out by, for example, pouring them in an alcohol solvent to cause precipitation.

Specific designing examples and application examples of the biotin polymer of the present invention will next be described.

For example, gelation of the polymer of the invention by using a crosslinking material facilitates designing or synthesis of a gel having biotin immobilized even inside of the gel. This also facilitates coating to a magnetic material or use as a separating material.

Molecular designing of a polymer having novel peculiarity can be attained by copolymerizing the biotin monomer with another monomer while considering the peculiarity of the biotin monomer.

For example, PNIPAM (poly-N-alkylacrylamide) is a known polymer (J. Macromol. Sci. Chem., $A_2$, 1441(1968)) exhibiting LCST (lower critical solution temperature). The copolymer obtained from N-isopropylacrylamide and the biotin monomer can acquire a molecule recognizing capacity without losing LCST characteristics.

Polymers having LCST (lower critical solution temperature) aggregate in the higher temperature side than the phase transition temperature and dissolves in the lower temperature side. They have therefore found widespread utility in various separating agents, medicament release control, artificial muscle, sensor, actuator, carrier for cell cultivation and the like.

No particular limitation is imposed on the monomer component usable in the invention for a polymer exhibiting LCST in an aqueous solution. Specific examples include poly(meth)acrylamide derivatives such as poly(N-methyl (meth)acrylamide), poly(N-ethyl (meth)acrylamide), poly (N-propyl (meth)acrylamide), poly(N-isopropyl (meth)acrylamide), poly(N-butyl (meth)acrylamide), polyl(N-acryloyl pyrrolidone), poly(N-acryloyl morpholine), poly(N,N-dimethyl (meth)acrylamide) and poly(N,N-diethyl (meth)acrylamide), poly-N-vinylamide derivatives such as N-vinylacetamide, N-vinylbutylamide and N-vinylisobutylamide, polyvinyl acetate partial hydrolyzate derivatives, methyl cellulose derivatives and alkyl vinyl ether derivatives such as poly(methyl vinyl ether) and poly(ethyl vinyl ether).

It was found that polymers obtained by copolymerization of acrylamide or methacrylamide with the biotin monomer of the invention exhibits UCST (upper critical solution temperature) characteristics in each of an aqueous solution and physiological saline.

The polymer derivatives having UCST (each of which may hereinafter be called "UCST polymer" simply) are preferably those obtained by charging the acrylamide or methacrylamide and the biotin monomer of the invention at a ratio (molar ratio) of the former to the latter ranging from 3 to 30. The UCST can be measured by dissolving the resulting polymer in water or saline, pouring the solution in a quartz cell, exposing its light channel to a light from a light source of 500 nm and studying the relation between the transmittance and temperature.

Fields to which these UCST polymers can be applied as a temperature-stimuli-sensitive polymer are presumed to be similar to the above-described ones. Different from LCST polymers, however, they dissolve on the high temperature side and aggregate on the low temperature side. There is accordingly a possibility of the development of materials which can be applied to the fields different from the above-described ones of the LCST polymers and they are therefore expected as a product attractive as a stimuli-sensitive material.

Particularly in a carrier for cell culture on a film containing an UCST polymer which aggregates on a low temperature side, the cultured cells on the carrier covered with the UCST polymer can be separated from the carrier at a low temperature (Tissue Culture, 17(9), 349–353(1990)). The polymer bonded to a medicament, both existing in a solution on a high temperature side, forms an aggregated polymer under a low temperature environment, whereby the medicament is enclosed inside of the polymer. In short, medicament release control is conducted ("Macromolecules, 27, 947–952(1994)").

In the invention, a hydrophilic or hydrophobic monomer can be incorporated in the polymer compound as a copolymer component. This makes it possible to change the LCST or UCST in an aqueous solution. The term "hydrophilic" or "hydrophobic" as used herein means hydrophilic or hydrophobic to a monomer to be a main component of the polymer.

Although the kind of the hydrophilic or hydrophobic monomer depends on the relation with the monomer to be a main component as described above and examples of it cannot be given in a wholesale manner, specific examples of the hydrophilic monomer include acrylic acid, methacrylic acid, acrylamide and methacrylamide, while those of the hydrophobic monomer include acrylates, methacrylates, vinyl chloride, vinylidene chloride and styrene.

No particular limitation is imposed on the molecular weight of the polymer compound of the invention. The properties such as UCST or LCST of the polymer compound do not depend much on the molecular weight. Practically, the weight-average molecular weight is about 500 to 1,000,000, more preferably about 1,000 to 100,000.

When used as a separating agent, the polymer compound preferably has UCST or LCST of 0 to 50° C., especially 0 to 40° C.

In the invention, the narrower the range of LCST or UCST (switching range), the better. According to the invention, thermo-responsive polymers having LCST or UCST within a practical switching range of 5° C. or less can be obtained.

The biotin monomer of the invention is useful as a polymer material having a biofunction and it has widespread utility (see, for example, "Chemical Sensors, 12(1), 811 (1996)"). This is because biotin itself is a biofunctional material capable of recognizing a plurality of substances, more specifically, capable of not only recognizing the molecule of avidin but also binding to a protein such as collagen. In addition, it can be applied to wide fields such as affinity chromatography making use of a sandwich structure having avidin interposed therein and immunochemistry making use of the capacity of recognizing many antibodies.

Since the thermo-responsive polymer of the invention has (imino)biotin immobilized thereto, a ligand can be immobilized by using avidin-biotin affinity without formation of a covalent bond.

Alternatively, since avidin has four sites that recognizes biotin, one of the binding sites of avidin is used for the biotin-immobilized thermo-responsive polymer, while the remaining three biotin binding sites are usable for immobilization of any biotinylated antibody, biotinylated enzyme, biotinylated heat shock protein and the like.

By adjusting an avidin immobilized ligand in advance, it can be immobilized directly to a biotin immobilized thermo-responsive polymer.

Use of a monoclonal or polyclonal antibody for an immobilized ligand facilitates separation or concentration of microorganisms in an aqueous solution. Described specifically, after an avidinated or biotinylated monoclonal or polyclonal antibody for a specific microorganism is bound to the heat sensitive polymer of the invention, the resulting polymer is brought into sufficient contact with the microorganism in a solution. The solution is heated to cause aggregation of both the microorganism and thermo-responsive polymer, whereby the microorganism can be collected easily by decantation. For example, by binding biotinylated Salmonella bacteria to the thermo-responsive polymer, only Salmonella bacteria in a food suspension can be concentrated and separated easily. Thus, combination of the polymer with a proper antibody and a detection reagent can be applied to a microorganism detection kit or diagnostic product and the kit or product thus obtained has much improved sensitivity compared with the conventional one.

The thermo-responsive polymer of the invention bound to a biotinylated base pair of any nucleic acid is usable for purification, concentration or detection of a specific gene.

The target substance bound or adsorbed to the stimuli-sensitive material of the invention can easily be eluted by (1) an increase in the concentration of a salt, (2) a pH change (to acid or alkali), (3) addition of an inhibitor, substrate or the like, (4) addition of a modifier such as urea or SDS, (5) addition of an organic solvent, a metal ion or the like, or (6) a temperature change.

More specifically, the thermo-responsive type separating material of the invention can be used effectively for test agents of bacteria or residual pesticides, application to diagnostic products, separation of bioproducts such as microorganisms or cultured cells, activation and maintenance of a bio-reactive function by immobilization of an enzyme or molecular chaperone.

The biotin monomer of the invention having biotin immobilized thereon is sufficiently economical and efficient that enables industrial application.

EXAMPLES

The present invention will be described in greater detail below, but the invention should not be construed as being limited thereto.

Example 1

Synthesis of 2-biotinylethyl acrylate (Compound A)

At room temperature, 500 mg of biotin (Compound i, product of Merck & Co., Inc.), 200 mg of 2-hydroxyethyl acrylate, 20 ml of thionyl chloride and 20 ml of toluene were mixed. The resulting mixture was refluxed for 2 hours. The solvent was then distilled off under reduced pressure. The residue was subjected to column chromatography by using a chloroform-methanol solvent mixture. By removal of the solvent, 100 mg of 2-biotinylethyl acrylate (Compound A) was obtained as a powdery substance (yield: 14%).

NMR analysis clearly indicated the existence of the target compound A (in DMSO).

NH and acrylic group bonding H:5H, δ5.8–6, 6a, 3a, OCH$_2$: 6H, multi, δ4.1–4.3, 6α:1H, multi, δ3.1, 6β:1H, d, δ 2.8, CH$_2$:8H, δ1–1.6.

Example 2

Synthesis of N-biotinyl-N'-methacroyltrimethylene amide (Compound B)

In 300 ml of N,N-dimethylformamide (DMF) were dissolved 18 g of N-(3-aminopropyl)methacrylamide hydrochloride (Compound iii), 24 g of biotin and 30 g of triethylamine, followed by cooling to 0° C. To the reaction mixture, a solution obtained by dissolving 28 g of diphenylphosphoryl azide in 50 ml of DMF was added dropwise over 1 hour. After completion of the dropwise addition, stirring was conducted at 0° C. for 3 hours and then at room temperature for 12 hours. After completion of the reaction, the solvent was distilled off and the residue was subjected to column chromatography by using a chloroform-methanol mixture as a developing solvent. As a result, 22 g of N-biotinyl-N'-methacroyltrimethylene amide (Compound B) was obtained as the target compound in the form of a white powder (yield: 59%).

NMR analysis clearly indicated the existence of the target compound B (in DMSO).

CONH:2H, br.s, δ7.9, NH, NH:2H, d, δ6.4, H2, H3:2H, s, δ 5.6, δ 5.3, 3a, 6a:2H, br.d, δ 4.2, CH$_2$:4H, s, δ 3.0, 6α, 6β: 2H, multi, δ 2.8, 4H:1H, multi, δ 2.6, COCH$_2$:2H, br.s, δ 2.1, CH$_2$:3H, δ 1.8, CH$_2$:8H, δ 1.2–1.5.

Example 3

Synthesis of N-iminobiotinyl-N'-methacroyltrimethylene amide (Compound C)

In a similar manner to Example 2 except for the use of 18 g of N-(3-aminopropyl)methacrylamide hydrobromide instead of 18 g of the N-(3-aminopropyl)methacrylamide hydrochloride obtained in Example 2 and 24 g of iminobiotin instead of 24 g of biotin, 15 g of hydrobromide of N-iminobiotinyl-N'-methacroyltrimethylene amide (Compound C) was obtained (yield: 42%).

NMR analysis clearly indicated the existence of the hydrobromide of the target compound C (in DMSO). NH, NH:2H, d, δ 8.0–8.2, CONH:2H, br.s, δ 7.9, =NH.HBr:2H, s, δ 7.5, H2, H3:2H, s, δ 5.6, δ5.3, 3a, 6a:2H, br.d, δ 4.2, $CH_2$:4H, s, δ 3.0, 6α, 6β:2H, multi, δ 2.8, 4H:1H, multi, δ 2.6, $COCH_2$:2H, br.s, δ 2.1, $CH_3$:3H, δ 1.8, $CH_2$:8H, δ 1.2–1.5.

Example 4

Synthesis of biotinol acrylate (Compound D)

4-1) Synthesis of Biotinol (Compound 1v) from Biotin (Compound i):

Lithium aluminum hydride (1.96 g, 51.64 mmol) was added to 250 ml of dehydrated ether in portions, followed by stirring. A hot solution obtained by dissolving 1.96 g (8.02 mmol) of biotin (Compound i) in 50 ml of pyridine was added dropwise to the reaction mixture and they were stirred at room temperature for 30 minutes. After reflux for 30 minutes, the reaction was terminated. Excessive lithium aluminum hydride was crushed by water or the like. Pyridine was removed under reduced pressure. To the residue was added 6N hydrochloric acid to adjust its pH to approximately 2. The mixture was extracted with chloroform. Distillation of the solvent yielded a white powder. The white powder was recrystallized from methanol, whereby 1.6 mg of biotinol (Compound iv) was obtained (yield: 85%).

4-2) Synthesis of biotinol acrylate (Compound D) by the reaction of biotinol (Compound iv) with an acrylating agent:

Reaction Scheme 1

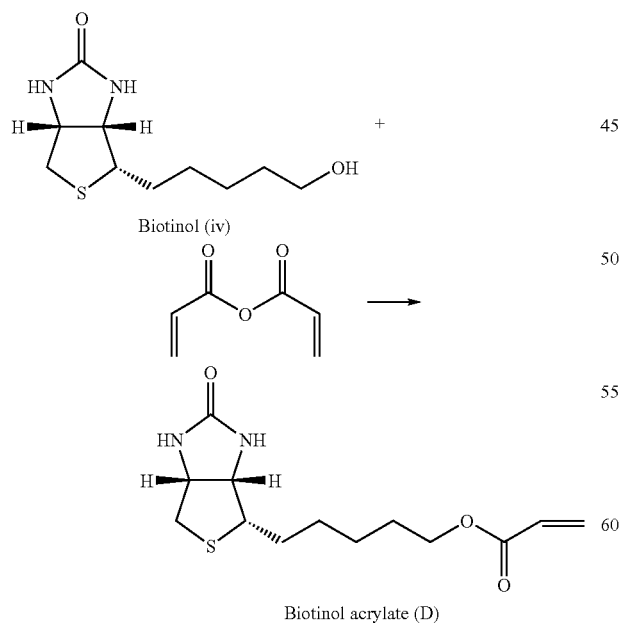

Biotinol acrylate (D)

After mixing 230 mg (1 mmol) of biotinol (Compound iv), 273 mg (3 mmol) of triethylamine, 252 mg (2 mmol) of acrylic anhydride, 12.9 mg (0.1 mmol) of dimethylaminopyridine and 5 ml of dichloromethane at room temperature, the mixture was refluxed. The reaction mixture was then washed with a saturated aqueous solution of $NaHCO_3$ and saturated saline and water. After completion of the reaction, the reaction mixture was extracted with a solvent, followed by column chromatography using a chloroform-methanol mixture as a developing solvent, whereby 170 mg of biotinol acrylate (Compound D) was obtained as white powder (yield: 59%, the yield of biotinol acrylate from biotin methyl ester was about 50%).

Results of NMR analysis and mass spectrometry (MS) clearly indicated the existence of the target compound D. NMR (in $CDCl_3$) H1,H2,H3: δ6.4-δ 6.1, H3:1H, d, δ 5.9, NH:1H, s, δ 5.6, δ 5.1, 6a:1H, multi, δ 4.5, 3a:1H, tri, δ 4.3, $OCH_2$:2H, tri, δ 4.1, H4:1H, multi, δ 3.1, 6α:1H, quart, δ 2.9, 6β:1H, d, δ2.6, $CH_2$:8H, δ 1–1.6.

MS mass=285

Example 5

Synthesis of biotinol methacrylate (Compound E)

After mixing 550 mg (2.3 mmol) of biotinol (Compound iv) obtained in Example 4, 1.4 g (7 mmol) of triethylamine ($Et_3N$), 1.6 g (4.6 mmol) of methacrylic anhydride, 60 mg of dimethylaminopyridine and 4 ml of dichloromethane (solvent), the mixture was refluxed. The reaction mixture was then washed with a saturated aqueous solution of $NaHCO_3$. After completion of the reaction, the reaction mixture was extracted with chloroform, followed by column chromatography by using a chloroform-methanol solvent mixture, whereby 630 mg of biotinol methacrylate (Compound E) was obtained as white powder (yield: 40%).

The results of NMR analysis and mass spectrometry (MS) clearly indicated the existence of the target compound E. NMR (in DMSO)NH:1H, s, δ 6.4, NH:1H, s, δ 6.3, H2, H3:1H, s, δ 6.0–5.6, 6a:1H, multi, δ 4.3, 3a, $OCH_2$:3H, multi, δ 4.1, 6α:1H, quart, δ 3.1, 6β:1H, d, δ 2.8, $CH_3$:3H, s, δ 1.9, $CH_2$:8H, δ1–1.6.

MS mass=300

Example 6

Synthesis of biotinamine acrylamide (Compound F)
Reaction scheme 2

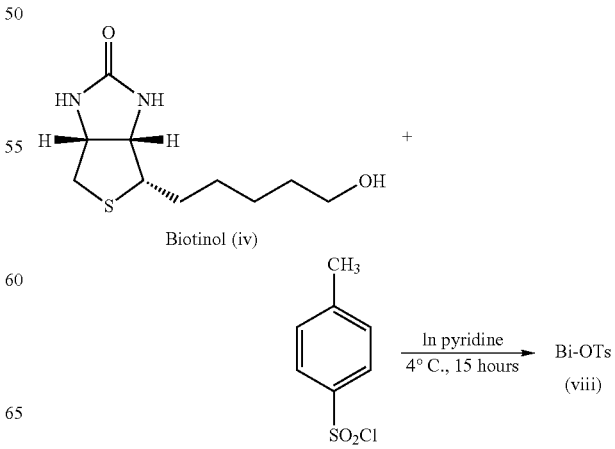

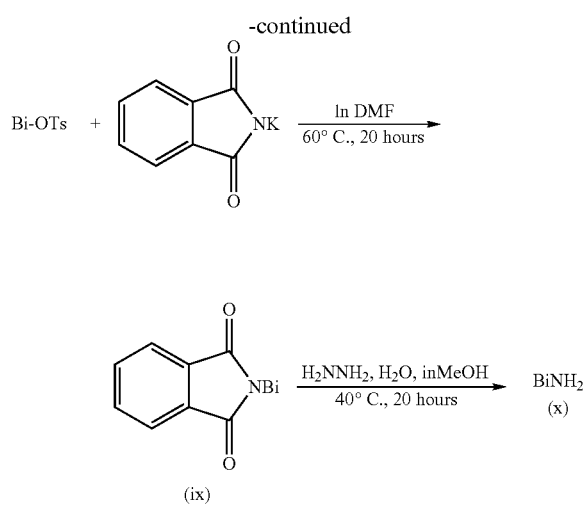

6-1) Synthesis of Biotinol Tosylate (Compound viii):

At 0° C., 1 g (4.3 mmol) of biotinol (Compound iv) obtained in Example 2 was added to a 25 ml dry pyridine solution having 2400 mg (12.6 mmol) of p-toluenesulfonyl chloride mixed therein. The resulting mixture was then allowed to stand at 0° C. for 15 hours. After reaction, the reaction mixture was poured into water, followed by extraction with dichloromethane. The solvent was removed, whereby 900 mg of biotinol tosylate (Compound viii) was obtained (yield: 54%).

6-2) Synthesis of a Biotin Phthalimide Derivative (Compound ix):

In 14 ml of dehydrated dimethylformamide (DMF) was dissolved 900 mg (2.3 mmol) of the biotinol tosylate (Compound viii) obtained above. To the resulting solution was added 481 mg (2.6 mmol) of phthalimide potassium salt and the mixture was heated at 60° C. for 20 hours. After completion of the reaction, water was poured to precipitate the phthalimide derivative. The derivative was collected by filtration and dried, whereby 570 mg of a biotin phthalimide derivative (Compound ix) was obtained (yield: 68%).

6-3) Synthesis of Biotinamine (Compound x):

Hydrazine monohydrate (626 mg) was added to methanol in portions (to give a 0.5M MeOH solution), followed by further addition of 570 mg of the biotin phthalimide derivative (Compound ix) obtained above. In a nitrogen atmosphere, the mixture was reacted at 40° C. for 20 hours, whereby 411 mg of unpurified biotinamine (BiNH$_2$) (Compound x) was obtained (yield: approximately 100%).

6-4) Synthesis of Biotinamine Acrylamide (Compound F):

In 4 ml of dimethylformamide (DMF; solvent) were dissolved 133 mg (0.5 mmol) of biotinamine hydrochloride obtained by the reaction of the above-described biotinamine (Compound x) with hydrochloric acid and 36 μl (0.5 mmol) of acrylic acid. The resulting solution was maintained at 0° C., followed by stirring. To the reaction mixture was added dropwise 165 μl (0.6 mmol) of diphenylphosphoryl azide (DPPA) and the mixture was maintained at 0° C. A solution obtained by dissolving 208 μl (1.5 mmol) of triethylamine in 1 ml of DMF was added dropwise and the mixture was stirred at 0° C. for 2 to 4 hours.

The reaction mixture was allowed to stand at room temperature and the reaction was continued overnight. After completion of the reaction, DMF was distilled off and the residue was extracted with chloroform. The chloroform layer was then washed with 1N hydrochloric acid, NaHCO$_3$ and water. The solvent was then removed. The residue was dissolved in a THF-n-hexane solvent mixture, whereby 40 mg of biotinamine acrylamide (Compound F) (yield: 25%) was obtained as a precipitate.

The results of NMR analysis and mass spectrometry (MS) clearly indicated the existence of the target compound F.

NMR (in DMSO)CONH:1H, s, δ 7.9, H1, H2, H3:3H, multi, δ7.5–6.9, NH, NH:1H, s, δ 6.4, δ6.3, 6a:1H, multi, δ 4.3, 3a:1H, multi, δ4.1, CONHCH$_2$, H4:3H, multi, δ3.5–3.0, 6α:1H, quart, δ2.8, 6β:1H, d, δ 2.5, CH$_2$:8H, δ 1–1.6.

MS mass=284

Example 7

Synthesis of biotinamine methacrylamide (Compound G)

In 5 ml of DMF (solvent) were dissolved 100 mg (0.38 mmol) of biotinamine hydrochloride and 38 μl (0.43 mmol) of methacrylic acid. The resulting solution was kept at 0° C., followed by stirring. To the reaction mixture was added dropwise 130 μl (0.5 mmol) of DPPA and the mixture was kept at 0° C. A solution obtained by dissolving 156 μl (1.1 mmol) of triethylamine in 1 ml of DMF was added dropwise and the mixture was stirred for 2 to 4 hours at 0° C. The reaction mixture was allowed to stand at room temperature and the reaction was continued overnight. After completion of the reaction, DMF was distilled off under reduced pressure. The residue was dissolved in chloroform. The chloroform layer was washed with 1N hydrochloric acid, NaHCO$_3$ and water. The solvent was then removed. The residue was dissolved in a THF-n-hexane solvent mixture, whereby 40 mg of biotinamine methacrylamide (Compound G) was obtained as a precipitate (yield: 35%).

Results of NMR analysis and mass spectrometry (MS) clearly indicated the existence of the target compound G. CONH:1H, s, δ 7.9, H1, H2, H3:3H, multi, δ 7.5–6.9, NH, NH:1H, s, δ 6.4, δ 6.3, 6a:1H, multi, δ 4.3, 3a:1H, multi, δ 4.1, CONHCH$_2$, H4:3H, multi, δ 3.5–3.0, 6α:1H, quart, δ 2.8, 6β:1H, D, δ 2.5, CH$_2$:6H, δ 1–1.6.

MS mass=299

Example 8

Synthesis of norbiotinamine acrylamide (Compound H)

In 3 ml of dimethylformamide (DMF; solvent) were dissolved 125 mg (0.5 mmol) of norbiotinamine hydrochloride (product of Merck & Co., Inc.) and 36 μl of acrylic acid. The resulting solution was kept at 0° C. and stirred. To the reaction mixture was added dropwise 165 μl (0.6 mmol) of diphenylphosphoryl azide (DPPA) and the mixture was kept at 0° C. A solution obtained by dissolving 208 μl (1.5 mmol) of triethylamine in 1 ml of DMF was added dropwise and the mixture was stirred at 0° C. for 2 to 4 hours.

The reaction mixture was kept at room temperature and reacted overnight. After completion of the reaction, DMF was distilled off. The residue was extracted with chloroform. The chloroform layer was then washed with 1N hydrochloric acid, NaHCO$_3$ and water, followed by removal of the solvent. The residue was dissolved in a THF-n-hexane solvent mixture, whereby 30 mg of norbiotinamine acrylamide (Compound H) was obtained as a precipitate (yield: 20%).

The results of NMR analysis clearly indicated the existence of the target compound H (in DMSO).

NMR (in DMSO)CONH:1H, s, δ 7.8, NH, NH:1H, s, δ 6.4, δ 6.3, H1, H2:1H, s, δ 5.6, δ 5.3, 6a:1H, multi, δ 4.3, 3a:1H, multi, δ 4.1, CONHCH$_2$, H4:3H, multi, δ 3.5–3.0, 6α:1H, quart, δ 2.8, 6β:1H, d, δ 2.5, CH$_3$:3H, δ 1.8, CH$_2$:8H, δ 1–1.6.

Example 9

Synthesis of norbiotinamine methacrylamide (Compound J)

In 3 ml of DMF (solvent) were dissolved 94 mg (0.38 mmol) of norbiotinamine hydrochloride and 38 μl (0.43 mmol) of methacrylic acid. The resulting solution was kept at 0° C. and stirred. DPPA (130 μl, 0.5 mmol) was then added dropwise to the reaction mixture and the temperature was kept at 0° C. A solution obtained by dissolving 156 μl (1.1 mmol) of triethylamine in 1 ml of DMF was added dropwise further and the mixture was stirred for 2 to 4 hours at 0° C. The reaction mixture was kept at room temperature and reacted overnight. After completion of the reaction, DMF was removed. The residue was extracted with chloroform. The chloroform layer was washed with 1N hydrochloric acid, NaHCO$_3$ and water, followed by removal of the solvent. The residue was dissolved in a THF-n-hexane solvent mixture, whereby 30 mg of norbiotinamine methacrylamide (Compound J) was obtained as a precipitate (yield: 30%).

The results of NMR analysis clearly indicated the existence of the target compound J (in DMSO).

CONH:1H, s, δ 7.8, NH, NH:2H, d, δ 6.4, H1, H2:1H, s, δ 5.6, δ5.3, 6a:1H, multi, δ 4.3, 3a:1H, multi, δ 4.1, CONHCH$_2$, H4:3H, multi, δ 3.5–3.0, 6α:1H, quart, δ 2.8, 6β:1H, d, δ 2.5, CH$_3$:3H, δ 1.8, CH$_2$:6H, δ 1–1.6.

Example 10

Synthesis of biotinolmethacroyl carbamate (Compound K)

In 20 ml of methylene chloride was dissolved 266 mg of methacroyl isocyanate (Compound vii). The solution was kept at 0° C. A methylene chloride solution containing 500 mg of biotinol was then added dropwise in portions. The mixture was stirred for 1 hour and then at room temperature for 10 hours.

After completion of the reaction, 30 ml of a saturated aqueous solution of sodium bicarbonate was added, followed by extraction with chloroform. From the chloroform layer, the solvent was distilled off under reduced pressure. The residue was subjected to chromatography on a silica gel column. The crude target compound thus obtained was recrystallized from isopropanol, whereby 120 mg of biotinolmethacroyl carbonate (Compound K) was obtained (yield: 16%).

The results of NMR analysis clearly indicated the existence of the target compound K.

CONHCO:1H, s, δ 8.4–8.5, NH:1H, s, δ 6.2, H2, H3:1H, s, δ 5.8, δ 5.6, NH:1H, s, δ 5.5, 6a:1H, multi, δ 4.5, 3a:1H, multi, δ 4.3, OCH$_2$:2H, tri, δ 4.2, 4H:1H, multi, δ 3.2, 6α:1H, quart, δ 2.9, 6β:1H, d, δ 2.7, CH$_3$:3H, s, δ 1.9, CH$_2$:8H, δ 1.2–1.7.

Protons of the above-described NMR data are indicated as follows:

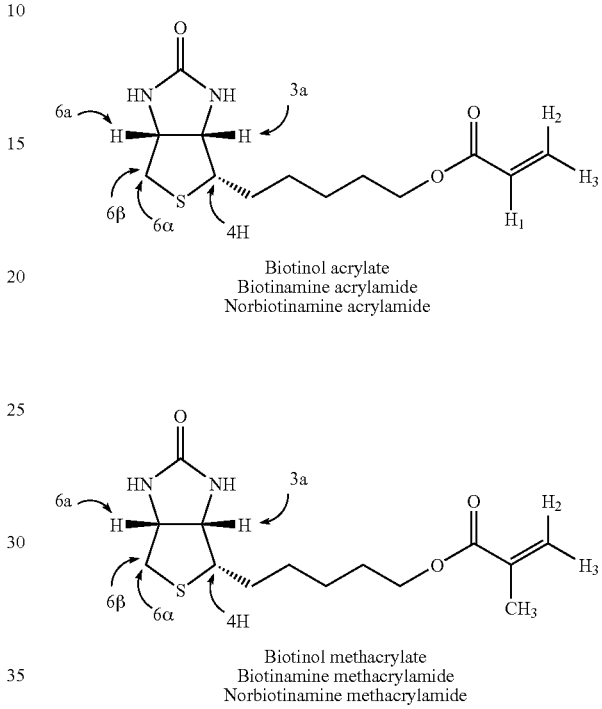

Biotinol acrylate
Biotinamine acrylamide
Norbiotinamine acrylamide

Biotinol methacrylate
Biotinamine methacrylamide
Norbiotinamine methacrylamide (In the case of amide, an oxygen atom is replaced by NH)

Examples 11 to 15

Synthesis of acrylamide/biotinol acrylate copolymers

Acrylamide (710 mg), 142 mg of biotinol acrylate (Compound B), 10 ml of dimethylsulfoxide and 8.5 mg of 2,2'-azobis(2,4-dimethylvaleronitrile) were mixed, followed by deaeration in a nitrogen gas atmosphere. The temperature was increased gradually and at 45° C., the reaction was effected for 2 to 3 hours under stirring. Finally, the temperature was increased to approximately 65° C., whereby the reaction was completed. Several ml of a solvent (dimethylsulfoxide) was added to the reaction system. Addition of the resulting mixture to ethanol caused precipitation (yield: at least 95%). After drying the precipitate, it was dissolved in water, followed by dialysis. By removal of water, purification of the polymer was completed.

The results of polymers obtained by polymerizing the acrylamide and biotinol acrylate charged at varied ratios (molar ratios) in the presence of either one of two initiators (use of azobisisobutyronitrile instead of the above-described initiator, 2,2'-azobis(2,4-dimethylvaleronitrile. They are different in the reaction temperature and molecular weight) are shown in Table-2.

TABLE 2

Temperature of measurement solution exhibiting 50% of transmittance with varied charging ratio (molar ratio) of acrylamide and biotinol acrylate to obtain copolymer

| | When 2,2'-azobis(2,4-dimethylvaleronitrile) is used as an initiator | | | | When azoisobutyronitrile is used as an initiator | | | |
|---|---|---|---|---|---|---|---|---|
| | Charged ratio AAm:BA | Transmittance Temperature of 50% solution (° C.) | | Weight-average molecular weight | | Charged ratio AAm:BA | Transmittance Temperature of 50% solution (° C.) | Weight-average molecular weight |
| Ex. 11 | 30:1 | 2 (water) | 2 (physiological saline) | 140,000 | Ex. 14 | 20:1 | 12 (water)  ~5 (physiological saline) | 32,000 |
| Ex. 12 | 20:1 | 18 (water) | 15 (physiological saline) | 89,000 | Ex. 15 | 10:1 | 45 (water)  50 (physiological saline) | 18,000 |
| Ex. 13 | 15:1 | 37 (water) | 28 (physiological saline) | 98,000 | | | | |

Molecular weight was measured using "G4000PW" of TOSO.
Physiological saline: Transmittance was measured in physiological saline.
Water: Transmittance was measured in distilled water.
Charged ratio: molar ratio
Polymerization temperature was 45 to 65° C. in the presence of 2,2-azobis(2,4-dimethylvaleronitrile).
Polymerization temperature was 80° C. in the presence of azobisisobutyronitrile.
Concentration of the solution used for measuring transmittance in Example 11 or 12: 6 mg/ml
Concentration of the solution used for measuring transmittance in water in Example 13: 10 mg/ml
Concentration of the solution used for measuring transmittance in physiological saline in Example 13: 6 mg/ml
Concentration of the solution used for measuring transmittance in Example 14: 22.4 mg/ml
Concentration of the solution used for measuring transmittance in Example 15: 6 mg/ml
AAm: acrylamide
BA: biotinol acrylate The NMR data (in DMSO) of the acrylamide/biotinolate copolymer (charged molar ratio 20:1) are shown below. Four peaks: δ 7.5–6.5, s: δ 6.4, s: δ 4.3, s: δ 4.1, s: δ 3.1, broad: δ 2.8, broad: δ 2.1, broad: δ 1.5–1.3.

The peaks were similar to the above ones in spite of a change in the charged ratio (molar ratio). The homopolymer of bitionol acrylate exhibited peaks at similar sites to the copolymer except about one peak at δ7.5 to 6.5.

It has thus been found that a copolymer containing the biotin monomer of the invention as a copolymer component has characteristics as a temperature stimuli-sensitive material.

Example 16

Synthesis of biotin immobilized poly(N-isopropyl acrylamide)

In a 300-ml flask were charged 0.488 g of N-isopropyl acrylamide, 0.159 g of N-methacroyl-N'-biotinyl propylenediamine and 94 ml of distilled water. The resulting mixture was stirred thoroughly at room temperature. To the reaction mixture was added 0.1 g of potassium persulfate, followed by stirring at room temperature for 6 hours. The reaction mixture was dialyzed for 24 hours, whereby a biotinylated poly(N-isopropyl acrylamide) solution having LCST was obtained. As a result of measurement, the resulting solution had a lower critical solution temperature (LCST) of 31° C. This LCST hardly changed even in physiological saline or a 100 mM phosphate buffer (pH 7.0). The polymer heated to the LCST or greater showed markedly high aggregation capacity and precipitated at the bottom. The polymer was collected by decantation.

The LCST was determined from transmittance of a visible light.

Example 17

Separation of avidin from the aqueous solution

After 50 μl of the aqueous poly(N-isopropyl acrylamide) solution obtained in Example 16, 50 μl of a 1.0% avidin solution, 100 μl of a 1.0M sodium phosphate buffer (pH 7.0) and 800 μl of distilled water were mixed thoroughly in a test tube, the test tube was placed in ice water to adjust the temperature of the solution to LCST or less. The aggregate was collected by decantation. After modification of 100 μl of the supernatant by SDS, disappearance of the band corresponding to avidin from the supernatant was confirmed by SDS-polyacrylamide gel electrophoresis (SDS-PAGE).

Example 18

Specific Separation of Avidin from Egg White

After 50 μl of the aqueous poly(N-isopropyl acrylamide) solution obtained in Example 16 and having LCST, 50 μl of a 1.0% avidin solution, 100 μl of a 1.0M sodium phosphate buffer (pH 7.0), 450 μl of distilled water and 400 μl of a 2.5% egg white solution were mixed thoroughly in a test tube, the test tube was placed in ice water to adjust the temperature of the solution to LCST or greater. The aggregate was collected by decantation. After modification of 100 μl of the supernatant by SDS, disappearance of the band corresponding to avidin from the supernatant was confirmed by SDS-PAGE.

Example 19

Immobilization of avidinated enzyme to biotin-immobilized poly(N-isopropyl acrylamide)

The aqueous poly(N-isopropyl acrylamide) solution obtained in Example 16 (100 μl), 1000 μl of a commercially available avidinated peroxidase solution (1 mg/ml), 100 μl of a 1.0M sodium phosphate buffer (pH 7.0) and 700 μl of distilled water were mixed thoroughly. The resulting solution was cooled and the aggregate was collected by decantation. After removal of 1900 μl of the supernatant, 1900 μl of a 0.1M phosphate buffer (pH 7.0) was added, whereby an aqueous poly(N-isopropyl acrylamide) solution having avidinated peroxidase immobilized thereto and exhibiting LCST was prepared. This solution exhibited solubility at temperatures not greater than LCST and aggregation at LCST or greater. The temperature of the solution was changed using a thermostat and operations such as dissolution, aggregation and collection by decantation were conducted. The peroxidase activity of each of the supernatants was measured by the peroxidase activity measuring method described below. Every time after collection by decantation, 1900 μl of the supernatant was removed and 1900 μl of a 0.1M phosphate buffer (pH 7.0) was added instead.

(Peroxidase Activity Measuring Method)

In the cell of an absorptiometer, 100 μl of 100 mM hydrogen peroxide, 50 mM phenol, 100 μl of 50 mM 4-aminoantipyrine, 100 μl of a 1.0M sodium phosphate buffer (pH 7.0) and 580 μl of distilled water were mixed in advance. To the resulting mixture was added 20 μl of a sample. After thorough mixing again, the resulting product was measured by an increase in the absorption at 500 nm. The above-described reaction was conducted at 30° C.

The measurement results of enzymatic activity of the supernatants after aggregating and dissolving operations were repeated by the above-described method are shown below in Table-3. The enzymatic activity was expressed by a specific activity relative to the activity upon first dissolution taken as 100.

TABLE-3

| Repetition (times) | Peroxidase activity (%) of aq. soln. of poly(N-isopropyl acrylamide) | Peroxidase activity (%) of the supernatant of poly(N-isopropyl acrylamide) after aggregation and collection |
|---|---|---|
| 1 | 100 | 8 |
| 2 | 99 | 4 |
| 3 | 99 | 3 |
| 5 | 98 | 3 |
| 10 | 100 | 2 |
| 20 | 102 | 0 |

These results suggest that the avidinated peroxidase immobilized to poly(N-isopropyl acrylamide) repeated dissolution and aggregation together with the poly(N-isopropyl acrylamide) and even by this repetition, did not lose its activity.

Example 20

Immobilization of a biotinylated enzyme to avidinated Poly(N-isopropyl acrylamide)

An avidinated poly(N-isopropyl acrylamide) whose avidin had three free biotin binding sites was obtained as described below. After addition of 500 μl of a 1.0% of an avidin solution, 100 μl of a 1.0M sodium phosphate buffer (pH 7.0) and 350 μl of distilled water to 50 μl of the aqueous poly(N-isopropyl acrylamide) solution obtained in Example 1 and thorough mixing in a test tube, the test tube was placed in a thermostat of 40° C. to adjust the temperature of the solution to LCST or greater. The aggregate was collected by decantation, whereby the avidinated poly(N-isopropyl acrylamide) whose biotin binding sites other than that bonded to the polymer were free was obtained. The resulting aqueous poly(N-isopropyl acrylamide) solution (100 μl), 1000 μl of a commercially available biotinylated peroxidase solution (1 mg/ml), 100 μl of a 1.0M sodium phosphate buffer (pH 7.0) and 700 μl of distilled water were mixed thoroughly. The resulting solution was cooled and from it, the aggregate was collected by decantation. After removal of 1900 μl of the supernatant, 1900 μl of a 0.1M phosphate buffer (pH 7.0) was added instead, whereby avidinated poly(N-isopropyl acrylamide) having biotinylated peroxidase immobilized thereto was prepared. As in Example 19, dissolution, aggregation and collection were repeated using this poly(N-isopropyl acrylamide). Measurement results of the enzymatic activity of each of the supernatants are shown below in Table-4. The enzymatic activity was expressed by a specific activity based on the activity upon first dissolution taken as 100.

TABLE-4

| Repetition (times) | Peroxidase activity (%) of aq. soln. of poly(N-isopropyl acrylamide) | Peroxidase activity (%) of the supernatant of poly(N-isopropyl acrylamide) after aggregation and collection |
|---|---|---|
| 1 | 100 | 1 |
| 2 | 101 | 1 |
| 3 | 100 | 1 |
| 5 | 98 | 0 |
| 10 | 97 | 0 |
| 20 | 95 | 0 |

These results suggest that the biotinylated peroxidase bonded to poly(N-isopropyl acrylamide) having avidin immobilized thereto repeated dissolution and aggregation together with poly(N-isopropyl acrylamide), and even by this repetition, did not lose its activity.

Example 21

Immobilization of a molecular chaperone to poly(N-isopropyl acrylamide)

Commercially available biotinylated Heat Shock Protein "HSP70" was mixed thoroughly with a 100 mM sodium phosphate buffer (pH 7.0). After modification of a 5 μl portion of the resulting mixture, the band of HSP70 was confirmed by SDS-PAGE. To the mixture was added 50 μl of the aqueous solution, obtained in Example 20, of avidinated poly(N-isopropyl acrylamide) whose biotin binding sites other than that with the polymer were free. After thorough mixing, the solution was heated as in Example 17 to aggregate the present compound. The compound was collected by decantation and HSP70 of the supernatant was confirmed by SDS-PAGE. As a result, HSP70 was not observed from the supernatant, which suggests its binding to the avidin immobilized to the poly(N-isopropyl acrylamide).

Example 22

Separation and concentration method of microorganisms

A commercially available biotinylated Salmonella antibody was immobilized to poly(N-isopropyl acrylamide) as in Example 19. The immobilization was confirmed by SDS-PAGE. To 20 ml of a bacterial suspension adjusted to contain 1 cell/ml of the Salmonella bacteria was added 1 ml of the resulting aqueous poly(N-isopropyl acrylamide) solution. After thorough stirring, the solution was heated as in Example 16 to aggregate poly(N-isopropyl acrylamide). The aggregate was collected by decantation and the supernatant was removed, whereby 1 ml of a solution was obtained. The resulting solution sterilized in advance was added to 20 ml of a Brain Heart Infusion agar medium which had been incubated in advance at 50° C. After prompt mixing, the mixture was spread on a Petri dish and was allowed to cool down until the agar solidified. At 37° C., incubation was conducted for 48 hours. The results of the colony count after 48 hours are shown below in Table-5. The above-described operations were all carried out in a clean bench. As a control, the vial count in 1 ml of the bacterial suspension which had been adjusted first was measured similarly without addition of poly(N-isopropyl acrylamide).

TABLE-5

|  | Control | Use of poly(N-isopropyl acrylamide) |
|---|---|---|
| Colony count | 1 | 21 |

From these results, it was apparent that the Salmonella bacteria were concentrated by the addition of the poly(N-isopropyl acrylamide) of the invention.

Example 23

Immobilization of nucleic acid to poly(n-isopropyl acrylamide)

To 500 µl (50 to 1000 bp) of commercially available biotin-labeled DNA fragments were added 450 µl of distilled water and 50 µl of the aqueous solution, which had been prepared in Example 20, of the avidinated poly(N-isopropyl acrylamide) whose biotin binding sites other than that with the polymer were free. After thorough mixing, the solution was heated as in Example 17 to aggregate poly(N-isopropyl acrylamide). The aggregate was collected by decantation. The agarose gel electrophoresis of the DNA fragments in the supernatant suggested that any one of the DNA fragments was bonded to poly(N-isopropyl acrylamide). A similar test was conducted for RNA and binding to poly(N-isopropyl acrylamide) was confirmed.

INDUSTRIAL APPLICABILITY

The polymerizable biotin derivatives (biotin monomers) of the invention have high polymerizability so that use of these monomers facilitates preparation of biotin-component-containing polymer derivatives usable in a variety of fields.

In particular, copolymerization of the monomer with another monomer makes it possible to synthesize or design a polymer equipped with functions of both monomers. By selecting a proper copolymer component or additive while making use of the effectiveness of the biotin component resulting from the biotin-avidin affinity, it is possible to synthesize or design various polyfunctional or multifunctional polymers having widespread utility.

For example, a copolymer of a biotin monomer and acrylamide or methacrylamide has UCST in each of an aqueous solution and physiological saline so that it serves as an attractive stimuli-sensitive material. A copolymer of a biotin monomer and a high-molecular weight monomer exhibiting LCST has markedly high aggregation force at LCST or greater so that reaction is conducted in a uniform system in an aqueous solution and after completion of the reaction, the ligand immobilized polymer aggregated by heating can be collected readily by filtration.

Use of these thermo-responsive polymers of the invention makes it possible to obtain excellent separating agents, test agents, immobilized enzymes and renaturing agents for denatured proteins.

The polymerizable biotin derivatives of the invention are monomers useful as a high molecular material having a biofunction and they can be used widely for immunoassay, biosensor, DNA operation, separating material and clinical therapy. This owes to that biotin itself is a biofunctional material capable of recognizing not only the molecule of avidin but also many antibodies and collagen. For example, the sandwich structure having avidin inserted thereto can be applied to various fields.

The polymer compound obtained using the polymerizable biotin of the invention can be produced industrially so that it is excellent in economy and efficiency.

What is claimed is:

1. A polymer compound which exhibits UCST (upper critical solution temperature) in an aqueous solution, the polymer compound comprising a polymerizable biotin derivative of formula (I) and acrylamide or methacrylamide as a copolymer component,

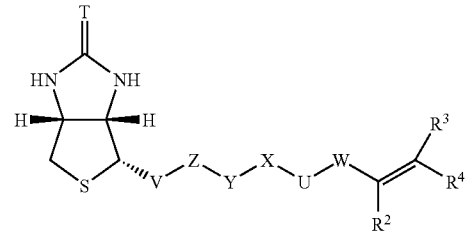

(I)

in formula (I), $R^2$ represents a hydrogen atom or an alkyl group; $R^3$ and $R^4$ each independently represents a hydrogen atom, an alkyl group or an aryl group;
T represents an oxygen atom or =NH;
W represents a single bond, a carbonyl group a thiocarbonyl group or a $C_{1-5}$ alkylene group; U represents a single bond or —NH—; X represents a single bond, a $C_{1-8}$ hydrocarbon bond, an oxygen atom or —NH—; Y represents a single bond, a carbonyl group, a thiocarbonyl group, —NH—, a 1,2-dioxyethylene group or a 1,2-diaminoethylene group; Z represents a single bond, a carbonyl group, a thiocarbonyl group, a $C_{1-5}$ alkylene group, an oxygen atom or —NH—; and V represents a single bond or a $C_{1-5}$ alkylene group,
wherein the polymer compound has a weight-average molecular weight of about 500 to 1,000,000, and the molar ratio of acrylamide or methacrylamide to biotin is from 3 to 30.

2. The polymer compound according to claim 1, further comprising a hydrophilic monomer selected from the group consisting of acrylic acid, methacrylic acid, acrylamide and methacrylamide, or hydrophobic monomer selected from the group consisting of acrylates, methacrylates, vinyl chloride, vinylidene chloride and styrene, as another copolymer component.

3. The polymer compound according to claim 1, wherein a biotinated antibody is immobilized through an avidin immobilized antibody or a binding site of the avidin.

* * * * *